US00PP24559P3

(12) United States Plant Patent
Bautista

(10) Patent No.: US PP24,559 P3
(45) Date of Patent: Jun. 17, 2014

(54) ***ECHEVERIA* PLANT NAMED 'BCEC-07.001'**

(50) Latin Name: ***Echeveria puvinata* Rose**
Varietal Denomination: BCEC-07.001

(75) Inventor: Rodolfo Valdoz Bautista, Half Moon Bay, CA (US)

(73) Assignee: Bay City Flower Company, Inc., Half Moon Bay, CA (US)

( * ) Notice: Subject to any disclaimer, the term of this patent is extended or adjusted under 35 U.S.C. 154(b) by 212 days.

(21) Appl. No.: 13/200,062

(22) Filed: Sep. 15, 2011

(65) Prior Publication Data

US 2013/0074233 P1 Mar. 21, 2013

(51) Int. Cl.
*A01H 5/00* (2006.01)

(52) U.S. Cl.
USPC ..... Plt./373; Plt./263.1

(58) Field of Classification Search
USPC ..... Plt./373, 263.1
See application file for complete search history.

*Primary Examiner* — Kent L Bell

(74) *Attorney, Agent, or Firm* — James R. Cypher; Charles R. Cypher

(57) ABSTRACT

A plant variety of the *Echeveria* genus, having the varietal designation *Echeveria pulvinata* Rose 'BCED-07.001', with a spreading growth habit, showy appearance, and puberlent stems, leaves and sepals. Hairs at growing stem portions, and leaf and sepal tips and upper margins are R.H.S. 44 B (red group). The adaxial surfaces of the petals are R.H.S. 26 B (orange group). The abaxial surface of the petals are R.H.S. 34 B (orange-red group).

4 Drawing Sheets

Latin name of genus and species of the plant claimed: *Echeveria puvinata* Rose.

Varietal denomination: The new plant's varietal denomination is 'BCEC-07.001'.

BACKGROUND OF THE INVENTION

The present invention relates to a new and distinct variety of the Crassulaceae family, *Echeveria* genus. The new variety is named 'BCEC-07.001'.

SUMMARY OF THE INVENTION

The distinguishing characteristics of the new variety are retained by asexually reproduced, successive generations.

The plant was found by the inventor in a cultivated area of a commercial nursery where the inventor was growing *Echeveria pulvinata* Rose 'Ruby'.

The new variety possesses the commercially desirable characteristics of a spreading growth habit with dense foliage, and many relatively large flowers that at maturity are R.H.S. 34 B (orange-red group) on their abaxial surfaces and R.H.S. 26 B (orange group) on their adaxial surfaces.

The new variety differs from *Echeveria pulvinata* Rose 'Ruby' by virtue of the color of its foliage which is much redder due to the puberulent hairs that grows on the foliage. The hair at the leaf tips and margins of 'BCEC-07.001' is R.H.S. 44 B (red group). The leaf tips and margins of 'Ruby' are also puberulent, but overall the leaves do not appear nearly as red. The hair at the leaf tips and margins of 'Ruby' is R.H.S. 43 A (red group). The raceme of 'Ruby' is also more corymb like with more buds that are more closely spaced along the raceme. The leaves of 'Ruby' are also generally longer and narrower, being 60 mm long, by 20 mm wide, by 3 mm thick, compared to the leaves of 'BCEC-07.001' which are 50 mm long, by 20 mm wide by 6 mm thick.

The inventor has asexually reproduced the new variety through three successive generations by cuttings at a commercial nursery in Half Moon Bay Calif., and has found that the combination of characteristics as herein disclosed remain firmly fixed.

BRIEF DESCRIPTION OF THE DRAWING

The accompanying drawings serve, by color photographic means, to illustrate the new plant variety. The colors are represented as truly as possible using conventional photographic procedures.

DETAILED DESCRIPTION OF THE NEW VARIETY

Figure 1:
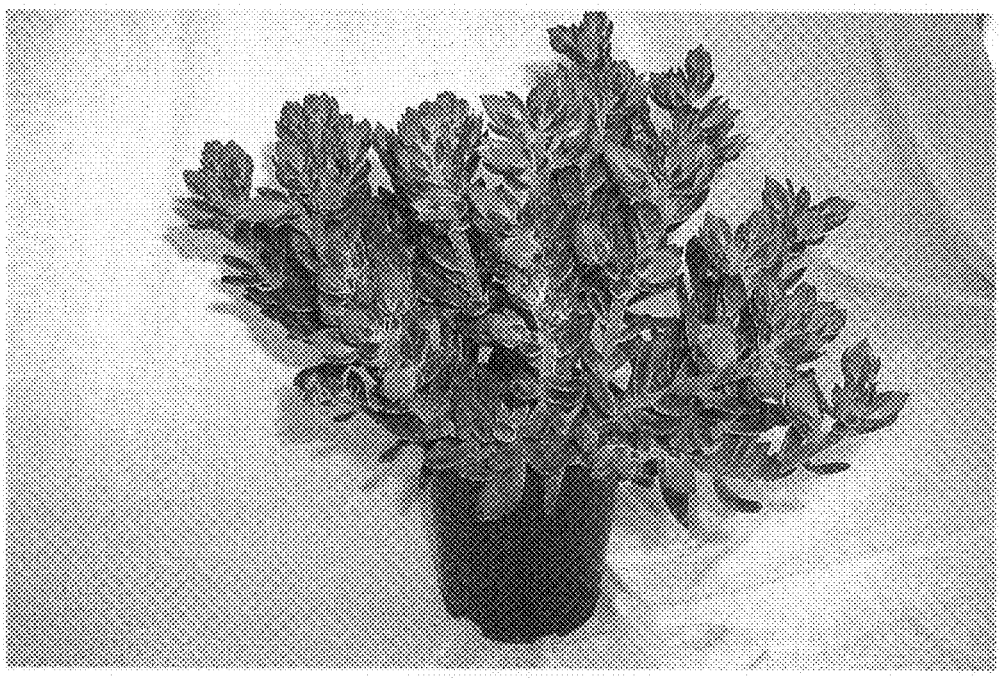
FIG. 1 is a color photograph of a plant grown from a cutting in one pot of the new variety illustrating the overall appearance and form of the plant, and the abundance of blooms.
Figure 2:
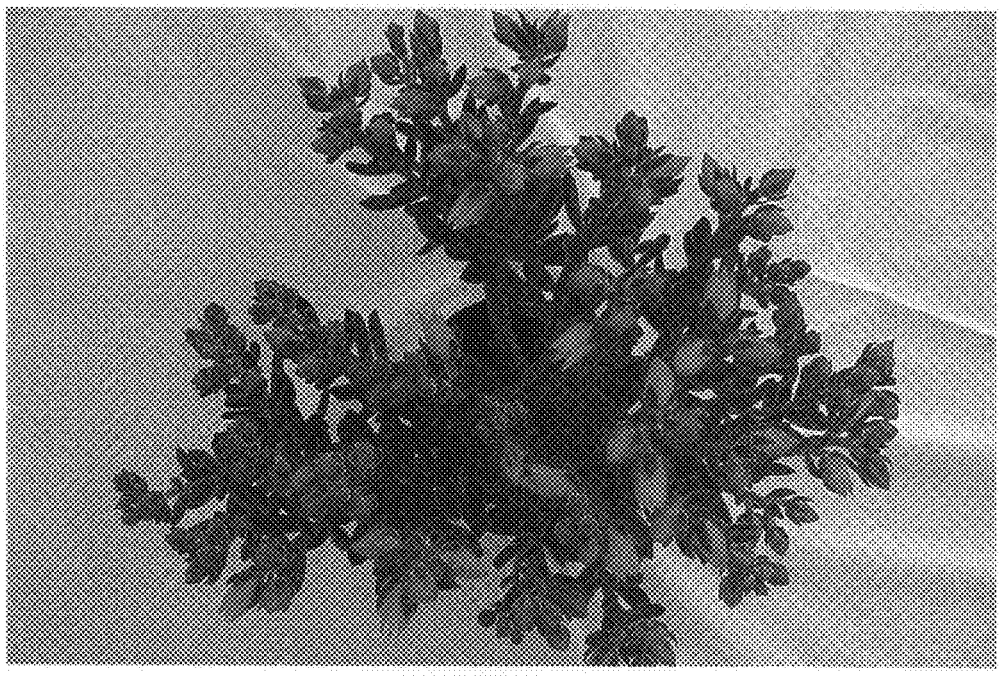
FIG. 2 is a color photograph of the plant showing the top of the plant.
Figure 3:
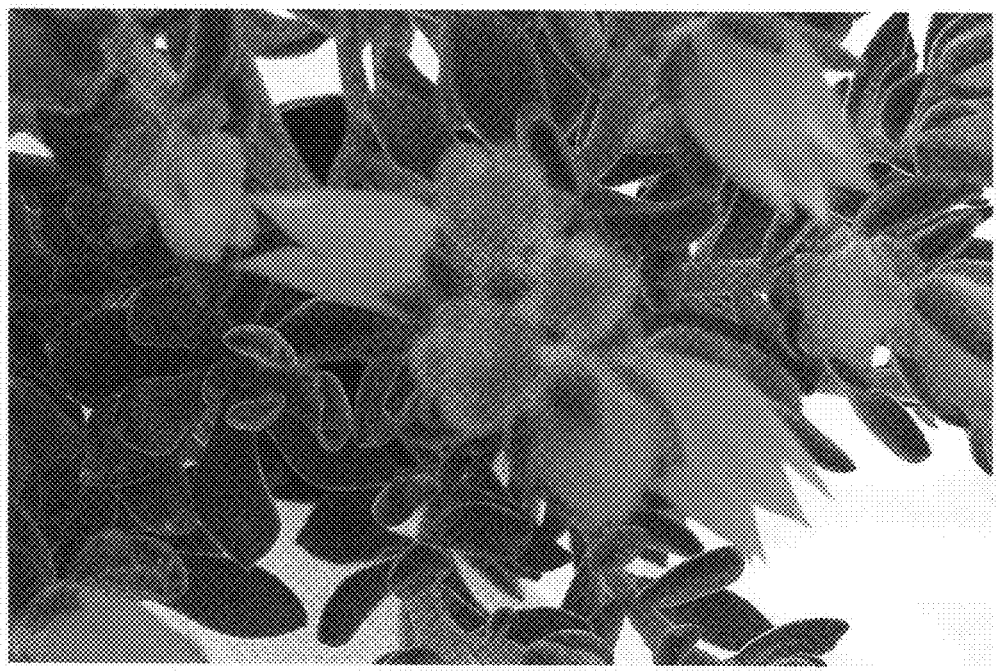
FIG. 3 is a close-up, color photograph of the top of the plant showing a primary rosulate stem in detail.
Figure 4:
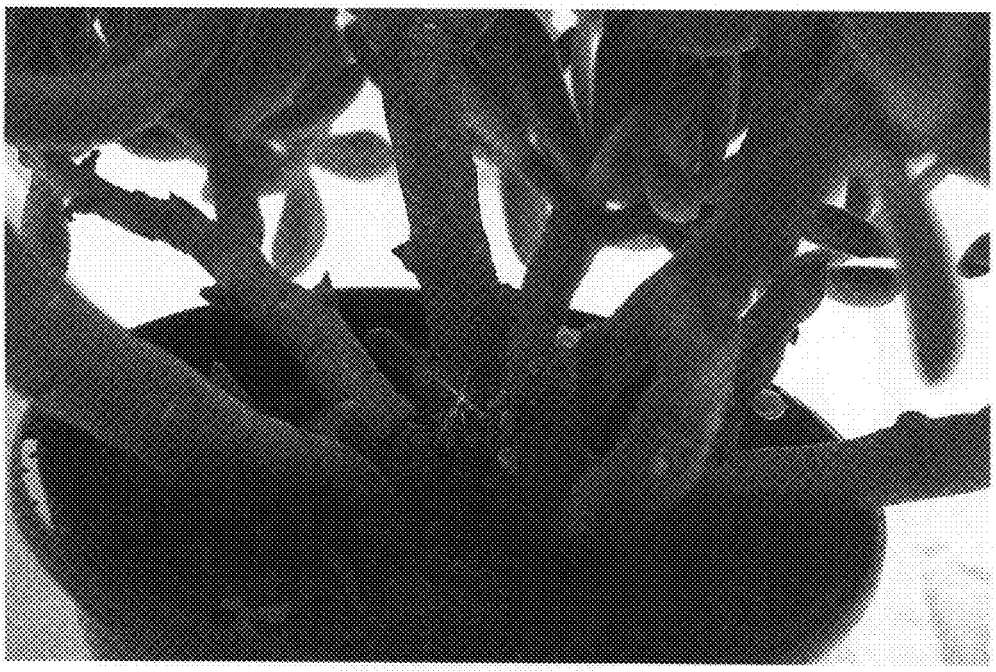
FIG. 4 is a color photograph of the base of a plant.
Figure 5:
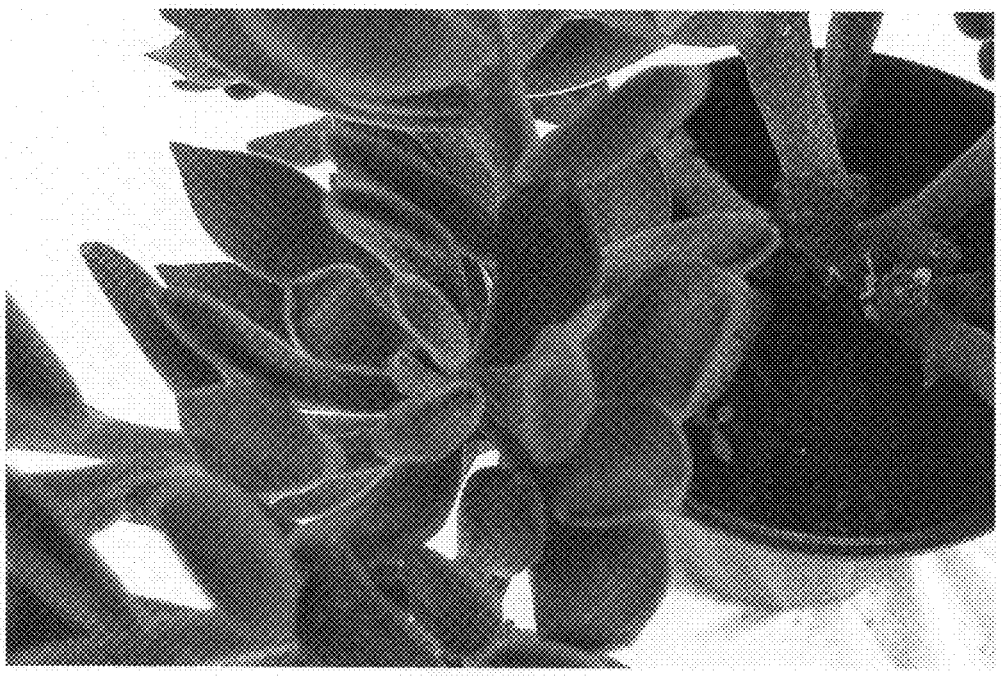
FIG. 5 is a close-up, color photograph of a primary rosulate stem in detail. The base of the plant can also be seen.
Figure 6:
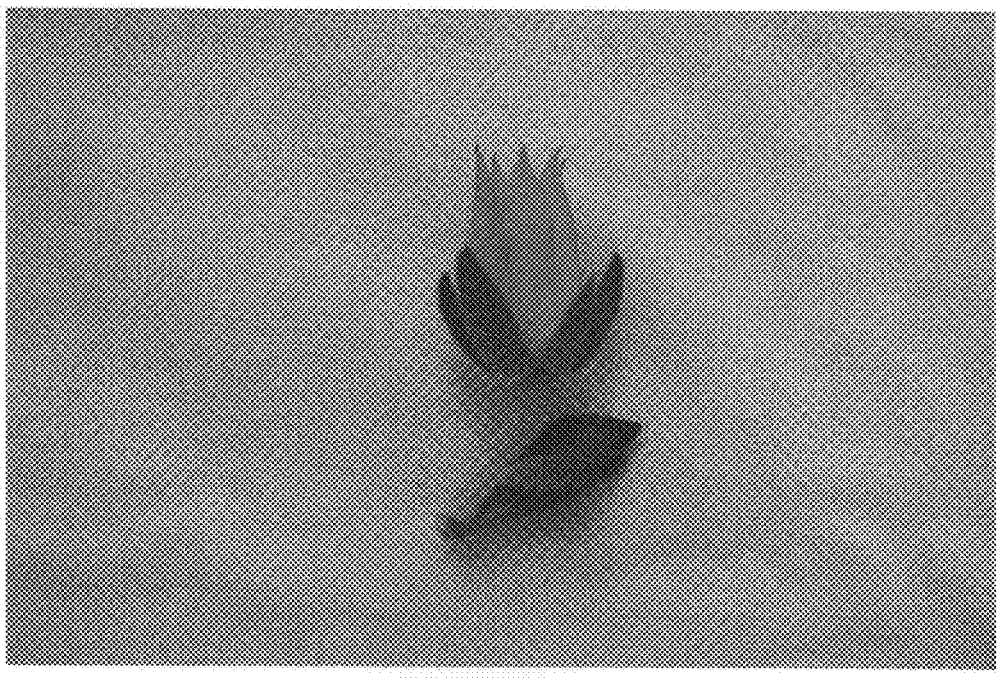
FIG. 6 is a close-up view of a flower removed from the plant.
Figure 7:
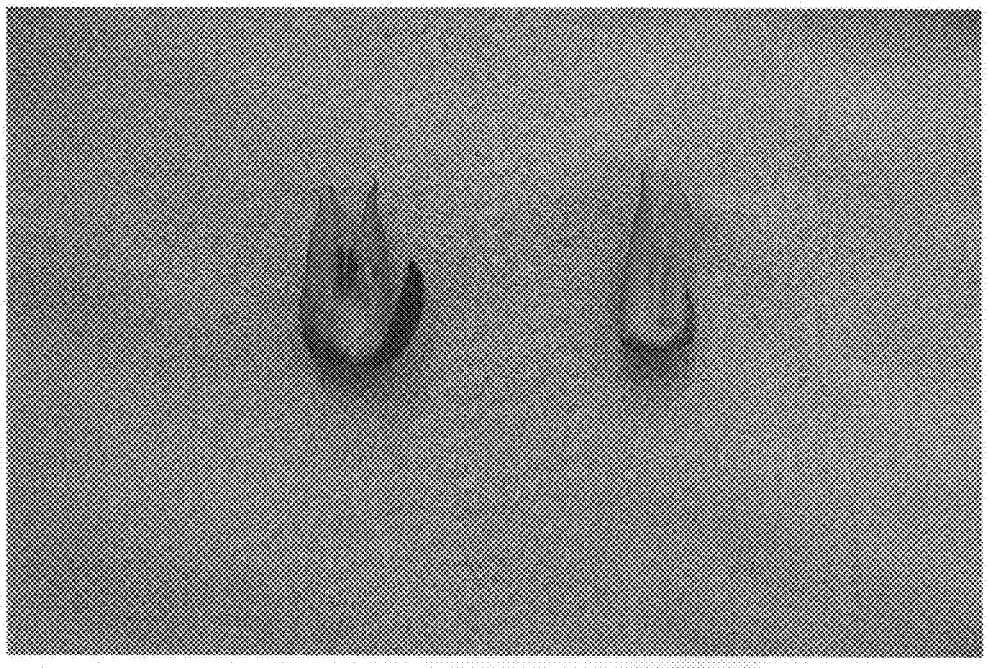
FIG. 7 is a close-up view of the halves of a flower that has been sectioned.

The following is a detailed description of the new variety. The new variety has not been observed under all possible environmental conditions. Color designation and other values stated may deviate slightly from the stated values from flowering to flowering, but the deviations will be within the range expected from varying environmental, seasonal and cultural conditions. Color designations were made according to The R.H.S. Colour Chart published by The Royal Horticultural Society of London, England.

The pictured plant was grown in a 4 inch pot.

The following description is based on observations of optimally fertilized plants grown at a commercial nursery in Half Moon Bay, Calif. Temperatures in Half Moon Bay on average range from 55 to 65 degrees Fahrenheit in the summer months, and from 45 to 55 degrees Fahrenheit in the winter months.

DETAILED PLANT DESCRIPTION

Varietal name: 'BCEC-07.001'.

Classification:

*Family*.—Crassulaceae.

*Genus and species*.—*Echeveria pulvinata* Rose.

Form: Succulent, terrestrial plant. Relatively short rosulate primary stems with racemes born on longer axillary branches. Each axillary branch has a flowering raceme, and multiple axillary branches are formed on each primary stem. The observed plants were approximately 23 cm high and 30 cm in diameter. Racemes on axillary branches are approximately 15 cm in length. Most flowers occur at the top of the raceme, but flowers can be found at the base and middle portions of the raceme as well.

Stems:

*General*.—Stems branch easily when pinched. Lateral branches are relatively long when compared to the main stem. Lateral branches of new growth from the rosette on the main stem are typically 15 cm in length. Older basal stems are 1 cm in diameter and mostly devoid of leaves. Older basal stems are puberlent and R.H.S. 201 C (grey group) with hairs that are R.H.S. 177 A (greyed-orange group). Young stems near apex of racemes are R.H.S. 138 A (green group) and are densely pubescent. Where the stem is growing the hairs are R.H.S. 44 B (red group). Stems are 3 mm in diameter below uppermost flowers.

Leaves:

*General*.—Leaves densely whorled, rosulate on primary stem, and are alternately whorled on the axillary stems or racemes with the separation of leaves ranging from 5 to 15 mm on the axillary stems. Leaves are simple, entire, fleshy and puberlent. They are oblanceolate to spatulate with broadly acuminate tips and have no petiole. Size: Length — 50 mm. Width — 20 mm wide. Thickness — 6 mm. Color: Adaxial and abaxial surfaces of leaves are predominately R.H.S. 138 A (green group). Hairs at leaf tips and margins are R.H.S. 44 B (red group). Texture — Abaxial and adaxial surfaces of the leaves are puberlent.

Flowers:

*General*.—Flowers are actinomorphic, hypogynous and 5-lobed with 10 stamens and a 5-loculed ovary. The calyx is deeply divided. The corolla is basally united, valvate to slightly imbricate, five-angled with erect lobes. Sepals and petals are both thick. Sepals are puberlent. Flower are 22 mm high with a diameter of 20 mm. Pedicel length between base of flower and raceme is 22 mm for a mature opened flower. Pedicels are 3 mm in diameter. Pedicels are R.H.S. 138 A (green group). Buds are oval and 15 mm high and 15 mm in diameter and are R.H.S. 44 B (red group) at their tips.

*Sepals*.—General: The calyx constitutes 5 deeply divided or separated, regular sepals that are ovate to lanceloate in shape. Margins are entire and tips are acute. Size: Length — 19 mm from base to tip of sepals when flower is mature. Width — 6 mm at their widest. Thickness — 3 mm. Color: Adaxial and abaxial surfaces of sepals are predominately R.H.S. 138 A (green group). Hairs at sepal tips and upper margins are R.H.S. 44 B (red group). Texture — Abaxial and adaxial surfaces of the leaves are puberlent.

*Petals*.—General: 5-lobed. Size: Length — 22 mm from base to tip of petals when flower is mature. Width — 7 mm at their widest. Thickness — 3 mm. Color: The adaxial surfaces of the petals are R.H.S. 26 B (orange group). The abaxial surface of the petals are R.H.S. 34 B (orange-red group). Texture: Succulent. Abaxial surface is sericous. Adaxial surface is glaucous.

*Androecium* (*stamens*).—General: 10 stamens, with 1 stamen inserted in detent of each petal. Stamens included in petals. Anthers basally attached. Size: Filament: Length — 14 mm. Width — 1 mm. Anther: Length — 5 mm. Width — 1 mm. Color: Anther is R.H.S. 151 B (yellow-green group). Filament is R.H.S. 12 B (yellow-green group).

*Gynoecium* (*pistil*).—General: Deeply divided 5-loculed exerted ovary. One style leading to 1 stigma per locule. Style shape — Elongated. Color — Top half of the style is R.H.S. 44 B (red group) and bottom half of the style is R.H.S. 146 C (yellow-green group). Size: Length — 9 mm long. Width — 1 mm. Ovary and Style color — R.H.S. 12 B (yellow-green group). Size: Length — 7 mm tall. Diameter — 4 mm.

Fragrance: none.

Blooming characteristics: When grown at a commercial nursery in San Mateo County in Northern California, the plant typically blooms between early August and mid-September, although the plant can be manipulated to bloom as late as early November. Flowers bloom — going from tight buds to open flower — in approximately 14 days. The flowers than slowly close again, but do not shrivel and drop from the plant for another four to six weeks. Temperature affects the longevity of the flowers.

I claim:

1. A new and distinct variety of *Echeveria* plant, substantially as herein shown and described.

* * * * *